United States Patent [19]

Weeks

[11] Plant 4,735

[45] Jun. 9, 1981

[54] ROSE PLANT

[76] Inventor: O. L. Weeks, 4759 Philadelphia St., Chino, Calif. 91710

[21] Appl. No.: 150,624

[22] Filed: May 16, 1980

[51] Int. Cl.[3] ..... A01H 5/00

[52] U.S. Cl. ..... Plt./11

[58] Field of Search ..... Plt./11, 18

*Primary Examiner*—Robert E. Bagwill

*Attorney, Agent, or Firm*—Vincent G. Gioia

[57] ABSTRACT

A new hybrid tea rose variety of salmon flower coloring and pale apricot tones remaining attractive as open blooms.

1 Drawing Figure

1

The present invention relates to a new and distinct variety of rose plant of the hybrid tea rose class, which was originated by my crossing an unnamed, unreleased and unpatented rose of my creation as seed parent and the rose known as "Arizona" as pollen parent.

Among the novel characteristics possessed by this new variety which distinguish it from its parents and all other varieties of which I am aware are salmon-colored blooms of good hybrid tea form developed from buds which appear bicolored and which mature into attractive open blooms with soft apricot-toned centers and lighter salmon-toned outer petals and a modestly vigorous plant with dark green foliage which contrasts attractively with the light colored flowers. Asexual reproduction by budding of the new variety as performed in San Bernardino County, Calif., shows that the foregoing and other distinguishing characteristics come true to form and are established and transmitted through succeeding propagations.

The new and improved rose variety which I have developed is a fine hybrid tea rose with salmon colored flowers borne single and in small clusters on a plant which is ideal where height control and disciplined contained landscaping is desired. The plant blooms freely outdoors and in the greenhouse on sturdy stems sufficient to support good sized flowers of 4 to 4½ inches diameter and good petalage. The softness of the flower color is emphasized by the plant's contrasting dark green foliage.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "24D" is plate 24D of the Royal Horticultural Society Color Chart.

Parentage: Seedling.

*Seed parent.*—Unnamed, unreleased seedling.

*Pollen parent.*—"Arizona".

Class: Hybrid tea.

The following observations are made of specimens grown outdors in San Bernardino County, Calif. during the month of October.

2

1. FLOWER

Blooming habit: Continuous.

A. Bud:

(1) *Size.*—Medium.

(2) *Form.*—Pointed, oval.

(3) *Color.*—Green bud shows greenish base and purplish bud tip. As sepals separate into flat star-like pattern, petals begin to unfurl and undersurface of outer petals have apricot to deep salmon coloring 24D to 26D whereas top surface of outer petals first show Egyptian Buff 19D. Shadings at bud center where the color intensity is the greatest approach 29B.

(4) *Sepals.*—Simple, occasionally fancy, longer length than green bud.

(5) *Peduncle.*—Length — medium. Aspect — straight. Strength — erect. Color — 138B.

B. Bloom:

(1) *Size.*—Average size when fully expanded — about 4 to 4½ inches.

(2) *Borne.*—Singly and in irregular clusters of two to three blooms.

(3) *Form.*—Relatively high centered slightly flaring with circular outline, petals loosely rolled outward.

(4) *Petalage.*—Number of petals under normal conditions — about 30 to 34.

(5) *Color.*—As bicolored buds unfurl, the gross color contrast of top and undersurface of outer petals becomes less evident and flowers at ⅓ to ½ open stage display more uniformly salmon color 27A to 27D since the undersurfaces of the centrally located petals are more similar to, although generally deeper toned than, the top surfaces of such petals. Apricot coloring may be seen when peering down into less opened flowers but soft apricot tones are visible at center of open blooms.

C. Petals:

(1) *Texture.*—Moderately thick.

(2) *Appearance.*—Generally soft satiny.

(3) *Form.*—Rounded with curved, sometimes slightly scalloped outer edge.

(4) *Arrangement.*—Regularly arranged.

(5) *Petaloids in center.*—Few.

(6) *Persistence.*—Drop off cleanly.

(7) *Fragrance.*—Slight.

(8) *Lasting quality.*—Long lasting on plant and as cut flower.

2. REPRODUCTIVE ORGANS

A. Stamens, filaments and anthers:
(1) *Arrangement.*—Many stamens regularly arranged about pistils tucked in calyx, filaments medium length most with anthers.
(2) *Color.*—Gold.
B. Pollen: Color — gold.
C. Styles: Uneven, medium, bunched.
D. Stigmas: Color — tan.
E. Hips: Nonobserved. 3.

3. PLANT

A. Form: Upright.
B. Growth: Modestly vigorous, well branching.
C. Foliage: Compound 3 to 7 leaflets.
(1) *Size.*—Medium.
(2) *Quantity.*—Abundant.
(3) *Color.*—New foliage: Greyed purple approaching 183B to 183C. Old foliage: Upper side — near to 136A. Under side — near to 138C.
(4) *Shape.*—Ovoid, mucronate.
(5) *Texture.*—Normal.
(6) *Edge.*—Serrated.
(7) *Serration.*—Normal.
(8) *Leaf stem.*—Color — near to 138B.

(9) *Stipules.*—Medium.
(10) *Resistance to disease.*—Mildew — good. Rust — good.
D. Wood:
(1) *New wood.*—Color — greyed green-greyed orange. Bark — smooth, shiny.
(2) *Old wood.*—Color — near 138B. Bark — smooth, shiny.
E. Thorns:
(1) *Thorns.*—Quantity (main stalk) — many. On laterals from stalk — many. Form — pointed slightly tipped downward. Length — medium to long. Color — tan to brown. Position — scattered.
(2) *Prickles.*—Many.
F. Winter hardiness: Good winter hardiness.

I claim:

1. A new and distinct variety of rose plant of the hybrid tea class, substantially as shown and described, characterized particularly by salmon colored flowers developed from buds which appear bicolored and which mature into attractive open blooms with soft apricot toned centers and lighter salmon-toned outer petals.

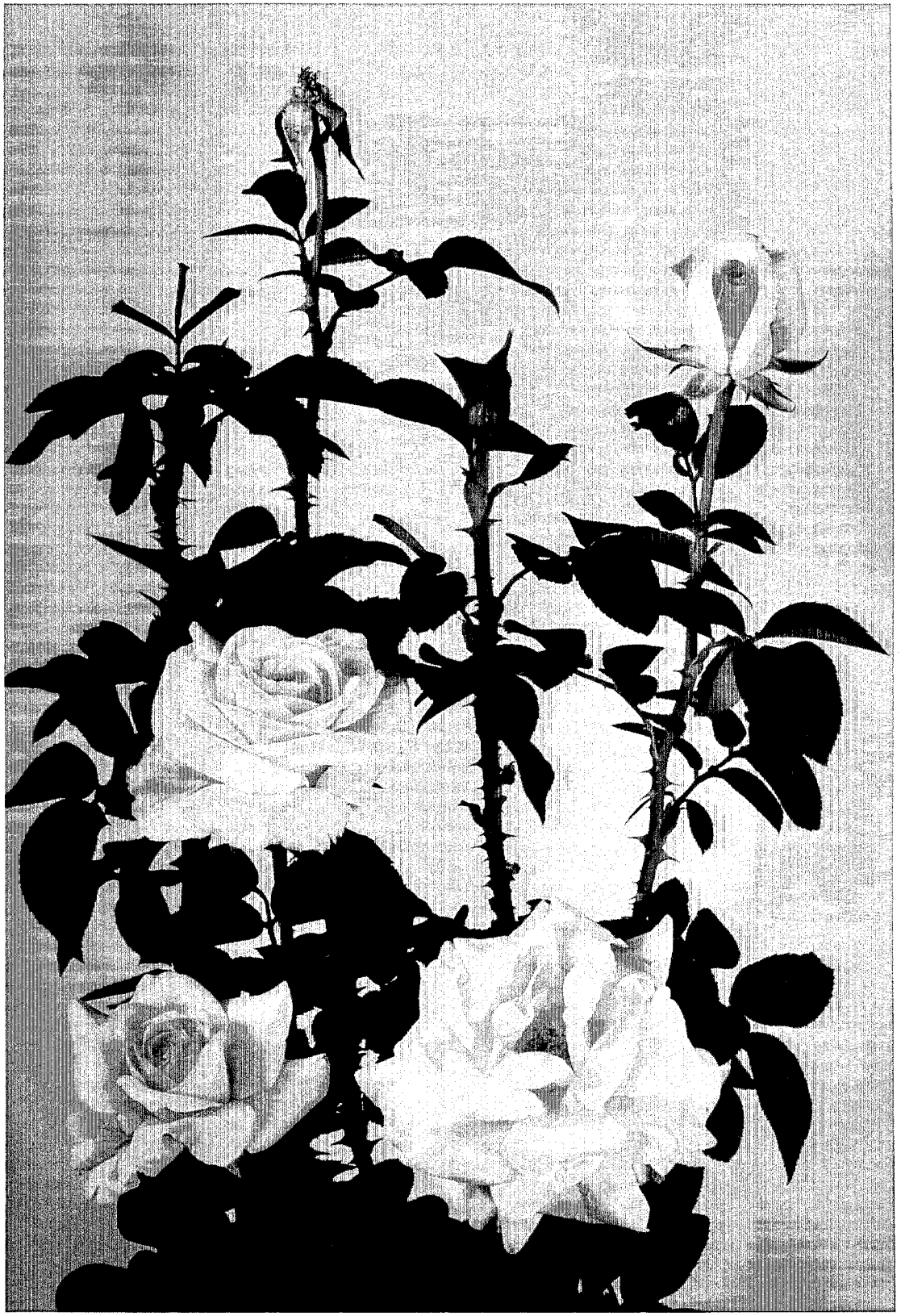

* * * * *